United States Patent
Shi et al.

(10) Patent No.: US 10,227,309 B2
(45) Date of Patent: Mar. 12, 2019

(54) CRYSTAL FORM A OF 1-ISOBUTYRYL-1'-((1-(4,4,4-TRIFLUOROBU-TYL)-4,5,6,7-TETRAHYDRO-1H-BENZO [D]IMIDAZOL-2-YL)METHYL)SPIRO[AZE-TIDINE-3,3'-INDOLIN]-2'-ONE

(71) Applicant: SHANDONG DANHONG PHARMACEUTICAL CO., LTD., Heze, Shandong (CN)

(72) Inventors: Weihua Shi, Shanghai (CN); Feng Xu, Shanghai (CN); Zheng Wang, Shanghai (CN); Weidong Li, Shanghai (CN); Linghui Wu, Shanghai (CN); Hongwei Li, Shanghai (CN); Minggao Zeng, Shanghai (CN); Kunmin Lai, Shanghai (CN); Zhigan Jiang, Shanghai (CN); Haiying He, Shanghai (CN)

(73) Assignee: SHANDONG DANHONG PHARMACEUTICAL CO., LTD., Heze, Shandong (CN)

( * ) Notice: Subject to any disclaimer, the term of this patent is extended or adjusted under 35 U.S.C. 154(b) by 0 days.

(21) Appl. No.: 15/580,167

(22) PCT Filed: Jun. 7, 2016

(86) PCT No.: PCT/CN2016/085104
§ 371 (c)(1),
(2) Date: Dec. 6, 2017

(87) PCT Pub. No.: WO2016/097908
PCT Pub. Date: Dec. 15, 2016

(65) Prior Publication Data
US 2018/0141915 A1    May 24, 2018

(30) Foreign Application Priority Data

Jun. 8, 2015   (CN) .......................... 2015 1 0309106

(51) Int. Cl.
| | | |
|---|---|---|
| *A61K 31/407* | (2006.01) | |
| *C07D 487/20* | (2006.01) | |
| *C07D 235/06* | (2006.01) | |
| *A61K 31/4184* | (2006.01) | |
| *C07D 487/10* | (2006.01) | |
| *A61P 31/12* | (2006.01) | |
| *B01D 9/00* | (2006.01) | |
| *C07B 41/06* | (2006.01) | |
| *C07B 43/04* | (2006.01) | |
| *C07D 209/96* | (2006.01) | |

(52) U.S. Cl.
CPC ........ *C07D 235/06* (2013.01); *A61K 31/4184* (2013.01); *A61P 31/12* (2018.01); *B01D 9/0004* (2013.01); *B01D 9/0054* (2013.01); *C07B 41/06* (2013.01); *C07B 43/04* (2013.01); *C07D 209/96* (2013.01); *C07D 487/10* (2013.01); *C07B 2200/13* (2013.01)

(58) Field of Classification Search
CPC ............................ A61K 31/407; C07D 487/20
USPC ........................................... 514/409; 548/411
See application file for complete search history.

(56) References Cited

U.S. PATENT DOCUMENTS

| 4,324,794 A | 4/1982 | Tidwell et al. |
| 5,256,668 A | 10/1993 | Hsu et al. |

FOREIGN PATENT DOCUMENTS

| AU | 1470497 A | 8/1997 |
| CN | 103347881 A | 10/2013 |
| EP | 0 581 46 A1 | 8/1982 |
| EP | 3081569 A | 10/2016 |
| JP | 2013-545786 | 12/2013 |
| JP | 2017-502951 | 1/2017 |
| WO | WO-99/38508 A1 | 8/1999 |
| WO | WO-00/04900 A1 | 2/2000 |
| WO | WO-2010/103306 A1 | 9/2010 |
| WO | 2012/080449 A | 6/2012 |
| WO | WO-2013/068769 A1 | 5/2013 |

(Continued)

OTHER PUBLICATIONS

"Update: Respiratory Syncytial Virus Activity—United States, 1996-97 Season," Journal of the American Medical Association, vol. 277, No. 1, 1997, pp. 12-13.

Chinese Patent Application No. 201510309106.4 with English translation.

Clercq, Erik, "Perspectives for the chemotherapy of respiratory syncytial virus (RSV) infections," International Journal of Antimicrobial Agents, vol. 7, 1996, pp. 193-202.

(Continued)

*Primary Examiner* — Douglas M Willis
(74) *Attorney, Agent, or Firm* — Foley & Lardner LLP

(57) ABSTRACT

Disclosed are a method for preparing an imidazole derivative and crystal form A and crystal form B thereof, and also disclosed is a method for preparing a compound of formula (I) and an intermediate thereof.

(I)

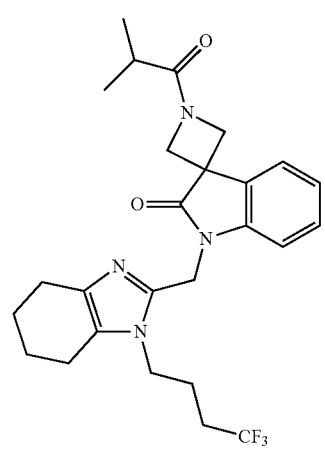

9 Claims, 3 Drawing Sheets

(56) References Cited

FOREIGN PATENT DOCUMENTS

| WO | WO-2014/060411 A1 | 4/2014 |
| --- | --- | --- |
| WO | WO-2015/085844 A1 | 6/2015 |
| WO | 2015/158653 A | 10/2015 |
| WO | 2016/055780 A | 4/2016 |
| WO | WO 16/197908 | * 12/2016 |

OTHER PUBLICATIONS

Dubovi et al., "Inhibition of Respiratory Syncytial Virus-Host Cell Interactions by Mono- and Diamidines," Antimicrobial agents and Chemotherapy, vol. 19, No. 4, 1981, pp. 649-656.

Roderick et al., "Bisbenzimidazoles. Potent Inhibitors of Rhinoviruses," Journal of Medicinal Chemistry, vol. 15, No. 6, 1972, pp. 655-658.

Shigeta et al., "Inhibitory effect of pyridobenzoazoles on orthomyxo- and paramyxovirus replication in vitro," Antiviral Chemistry & Chemotherapy, vol. 3, No. 3, 1992, pp. 171-177.

Wyde et al., "CL387626 exhibits marked and unusual antiviral activity against respiratory syncytial in tissue culture and in cotton rats," Antiviral Research, vol. 38, 1998, pp. 31-42.

International Search Report with English Translation and Written Opinion issued in corresponding application No. PCT/CN2016/085104 dated Sep. 14, 2016.

Partial European Search Report issued in corresponding application No. 16 806 806.2 dated May 4, 2018.

Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 2009, 19(16), 4857-4862.

The Extended European Search Report issued in European Patent Application No. 16806806.2 dated Aug. 30, 2018.

i Notification of Reasons for Refusal issued in Japanese Patent Application No. 2017-564539 dated Nov. 13, 2018.

* cited by examiner

CRYSTAL FORM A OF 1-ISOBUTYRYL-1'-((1-(4,4,4-TRIFLUOROBUTYL)-4,5,6,7-TETRAHYDRO-1H-BENZO[D]IMIDAZOL-2-YL)METHYL)SPIRO[AZETIDINE-3,3'-INDOLIN]-2'-ONE

CROSS REFERENCE TO RELATED APPLICATIONS

The present application is a National Stage application of PCT/CN2016/085104, filed Jun. 7, 2016, which claims priority from Chinese application no. 201510309106.4, filed Jun. 8, 2015.

BACKGROUND OF THE INVENTION

Field of Invention

The present invention relates to a method for preparing an imidazole derivative, crystal form A, crystal form B, and the corresponding preparation process thereof, the present invention also relates to a method for preparing an intermediate of the compound of formula (I).

Description of Related Art

Respiratory syncytial virus (RSV) is the main cause of severe lower respiratory tract infection in infants, children, the elderly and those with impaired immunity. Severe viral infections can cause bronchiolitis or pneumonia that require hospitalization or cause death (JAMA, 1997, 277, 12). Recently, Ribavirin has been approved for the treatment of the virus infection. Ribavirin is a nucleoside analog that is administered intranasally in the form of an aerosol. And the toxicity of the drug is considerable and its efficacy is controversial. In addition to ribavirin, RespiGam and Synagis are immunoglobulin and monoclonal antibodies neutralizing RSV, respectively. They are the two biological agents that have been approved for the prevention of RSV infection in high-risk children. RespiGam and Synagis are very expensive and require parenteral administration.

Many drugs are known to be useful in inhibiting respiratory syncytial virus (De Clercq, Int. J. Antiviral Agent, 1996, 7, 193). Y Tao et al. (EP0058146A1, 1998) revealed that the known antihistamine, cetirizine, showed anti-RSV activity. A series of amidino compounds as RSV inhibitors were reported by Tidwell et al. in J. Med. Chem. 1983, 26,294 (U.S. Pat. No. 4,324,794, 1982) and Dubovi et al. in Antimicrobial Agents and Chemotherapy, 1981, 19, 649. A series of 6-aminopyrimidones having anti-RSV antiviral activity were also disclosed by Hsu et al. in U.S. Pat. No. 5,256,668 (1993). A series of triazine-containing compounds for the treatment and/or prevention of RSV infection were disclosed by Y Gluzman et al. (AU Patent, Au-A-14, 704, 1997) and P. R. Wey et al. (Antiviral Res. 1998, 38, 31). Pyrido [1,2-a]benzopyrrole and pyrimido [1,2a] benzimidazole were disclosed by S. Shigeta et al. in Antiviral Chem. & Amp; Chemother. 1992, 3, 171. These compounds have been shown to inhibit the replication of the orthomyxovirus and paramyxovirus in HeLa cells. It was reported that bis-benzimidazoles with ethylene glycol linkages were also potent rhinovirus inhibitors (Roderick et al., J. Med. Chem. 1972, 15, 655). Other structurally related compounds were bis-benzimidazoles with antifungal activity (B. Cakir et al., Eczacilik Fak Derg. 1988, 5, 71). Recently, a series of benzimidazoles (WO 00/04900) for the treatment and prevention of RSV infection were discovered by Yu et al. In addition, Theodore Nitz also found a series of compounds of formula III (WO 99/38508) that inhibit RSV in Hep-2 cell tissue culture assays.

At present, BMS433771 is disclosed by BMS having a structure of general formula (B-1):

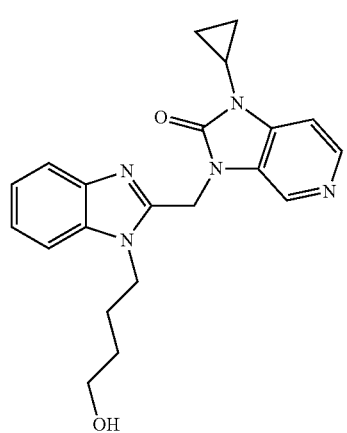

(B-1)

WO2013068769A1 of Viral discloses a class of compounds having the structural of general formula (B-II):

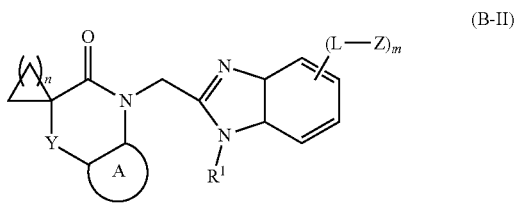

(B-II)

WO2014060411A1 of Janssen R & D Ireland discloses a class of compounds having a structure of (B-III) general Formula (R1):

Formula(R1)

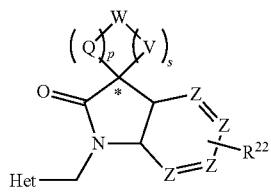

(B-III)

Wherein Het represents a heterocyclic ring such as structure (a), (b), (c) or (d), shown by formula (B-IV) in the formula X represents an aromatic ring containing at least two C atoms, or N atoms.

(B-IV)

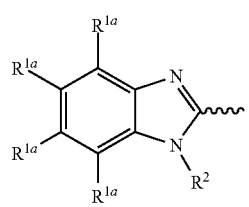

(a)

(b)
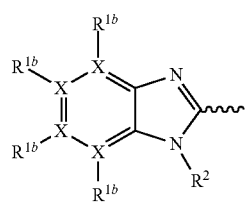

(c)
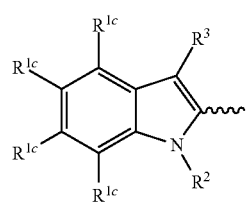

(d)
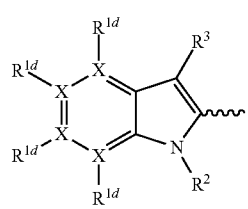

WO02010103306A1 of AstraZeneca discloses a class of compounds having a structure of general formula (B-V):

(B-V)
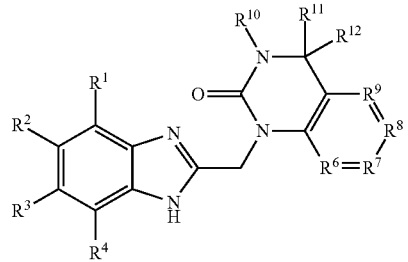

Although the above compounds present in the prior art can be used to inhibit respiratory syncytial virus, an improvement in activity and solubility, etc. is still required.

BRIEF SUMMARY OF THE INVENTION

The present invention provides a process for preparing a compound of formula (I):

(I)
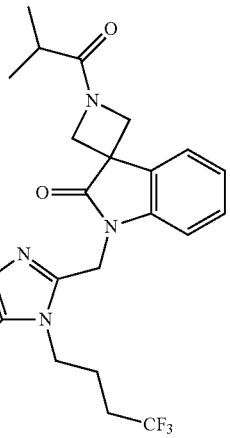

comprising the following step:

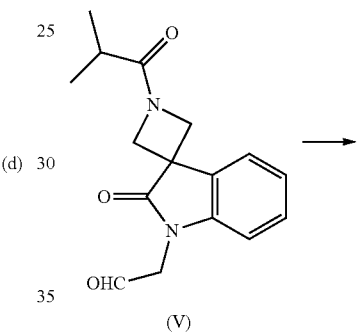

(V)

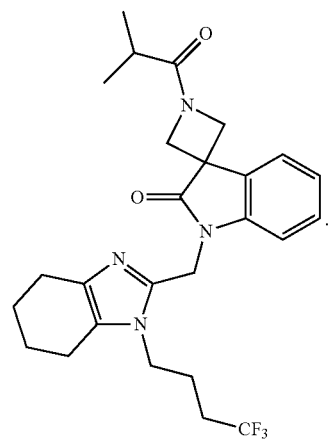

(I)

In some embodiments of the present invention, the above process comprises the following step:

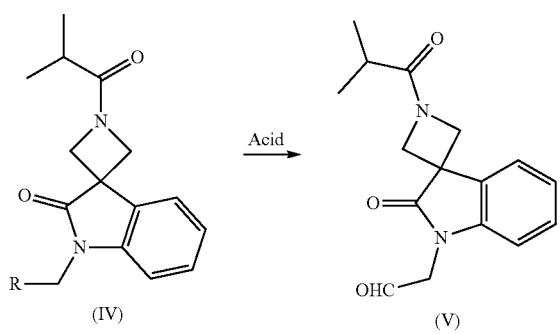

wherein, R is selected from

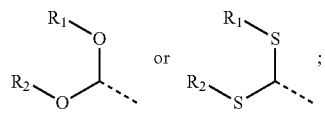

each of $R_1$ and $R_2$ is independently selected from a $C_{1-3}$ alkyl;

optionally, $R_1$ and $R_2$ are connected to the same atom to form a 5- to 6-membered ring optionally substituted by 1, 2, 3 or 4 of R'(s), R' is selected from methyl, ethyl, isopropyl or n-propyl;

the acid is selected from the group consisting of trifluoroacetic acid, acetic acid, hydrochloric acid, dilute sulfuric acid and p-toluenesulfonic acid.

In some embodiments of the present invention, the above R is selected from wherein, HA is selected from trifluoromethanesulfonic acid;

the insert solvent is a single solvent or a mixed solvent for several solvents selected from the group consisting of dichloromethane, ethyl acetate, isopropyl acetate, tetrahydrofuran, dioxane, 2-methyltetrahydrofuran, diethyl ether, methyl tert-butyl ether, pentane, n-hexane, cyclohexane, n-heptane and octane;

the weight ratio of the compound of the formula (VII) to the inert solvent is from 1:1 to 1:10.

In some embodiments of the present invention, the insert solvent is a single solvent or a mixed solvent for several solvents selected from the group consisting of ethyl acetate, isopropyl acetate, methyl tert-butyl ether, cyclohexane and n-heptane.

In some embodiments of the present invention, the insert solvent is a mixed solvent of ethyl acetate and n-heptane.

In some embodiments of the present invention, the process for preparing the compound of formula (I) comprises the following reaction route:

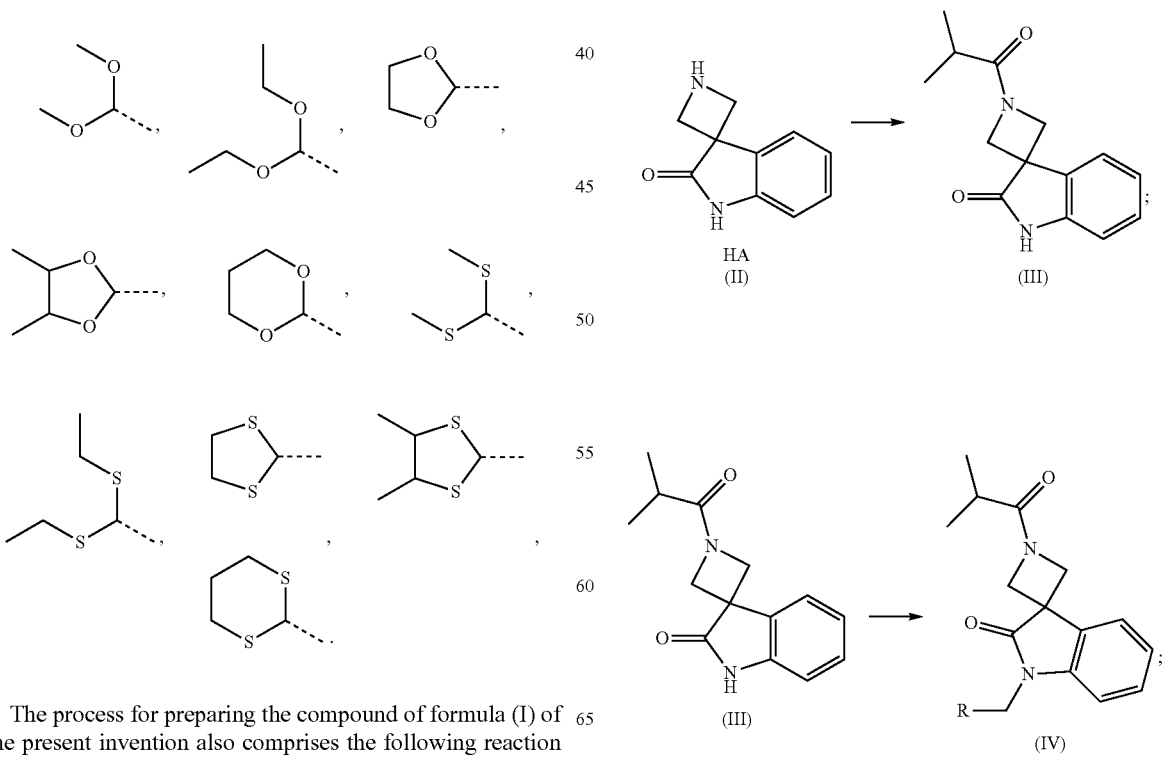

The process for preparing the compound of formula (I) of the present invention also comprises the following reaction route:

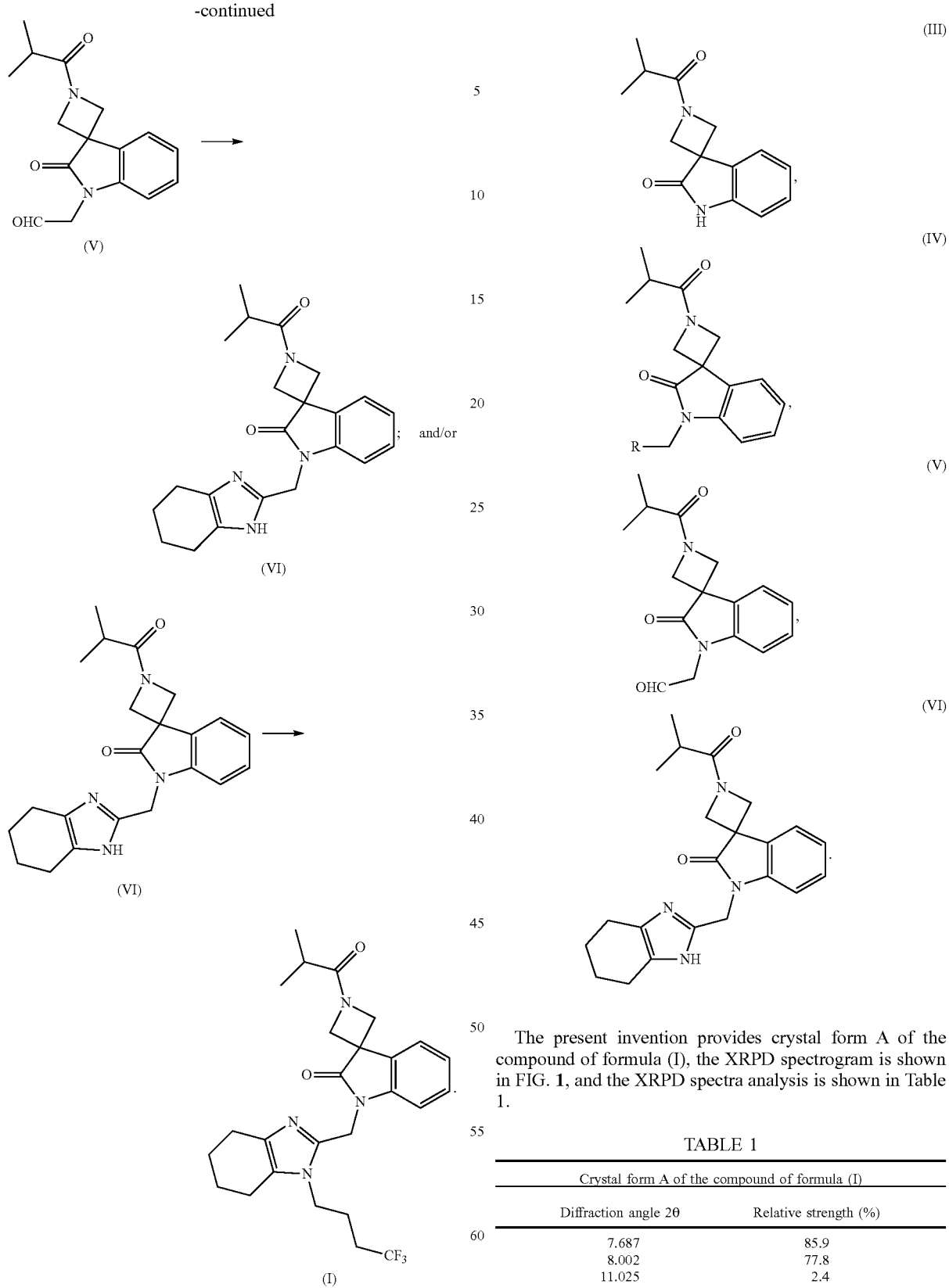

The present invention provides crystal form A of the compound of formula (I), the XRPD spectrogram is shown in FIG. 1, and the XRPD spectra analysis is shown in Table 1.

TABLE 1

| Crystal form A of the compound of formula (I) | |
| --- | --- |
| Diffraction angle 2θ | Relative strength (%) |
| 7.687 | 85.9 |
| 8.002 | 77.8 |
| 11.025 | 2.4 |
| 13.033 | 4.6 |
| 13.348 | 22.4 |
| 14.174 | 52.0 |
| 15.220 | 21.6 |
| 15.912 | 56.8 |

The present invention also provides a compound of the following formula as an intermediate for preparing the compound of formula (I):

TABLE 1-continued

Crystal form A of the compound of formula (I)

| Diffraction angle 2θ | Relative strength (%) |
|---|---|
| 16.678 | 4.1 |
| 17.213 | 42.5 |
| 17.646 | 29.8 |
| 19.168 | 34.4 |
| 19.557 | 29.3 |
| 19.979 | 2.7 |
| 21.315 | 100.0 |
| 21.632 | 9.5 |
| 22.083 | 38.4 |
| 22.615 | 4.4 |
| 22.987 | 4.0 |
| 23.271 | 8.2 |
| 23.898 | 96.6 |
| 25.101 | 82.5 |
| 25.538 | 4.3 |
| 25.888 | 9.1 |
| 26.796 | 11.4 |
| 28.037 | 5.6 |
| 28.434 | 32.0 |
| 29.815 | 20.9 |
| 30.682 | 4.6 |
| 31.076 | 2.6 |
| 31.474 | 4.6 |
| 31.925 | 8.5 |
| 33.738 | 2.4 |
| 34.667 | 2.3 |
| 36.938 | 2.9 |
| 37.704 | 4.9 |
| 38.513 | 2.4 |

The present invention provides crystal form B of the compound of formula (I), the XRPD spectrogram is shown in FIG. 2, and the XRPD spectra analysis is shown in Table 2.

TABLE 2

Crystal form B of the compound of formula (I)

| Diffraction angle 2θ | Relative strength (%) |
|---|---|
| 6.030 | 100.0 |
| 10.173 | 6.7 |
| 10.528 | 8.4 |
| 11.869 | 24.9 |
| 13.721 | 8.0 |
| 15.122 | 2.2 |
| 15.615 | 2.2 |
| 17.136 | 2.3 |
| 18.021 | 16.9 |
| 18.377 | 8.1 |
| 19.207 | 2.6 |
| 19.758 | 15.5 |
| 20.782 | 7.0 |
| 21.338 | 2.3 |
| 22.559 | 11.8 |
| 23.248 | 16.4 |
| 25.043 | 12.9 |
| 26.307 | 3.4 |
| 29.087 | 5.5 |
| 29.701 | 2.5 |

The present invention provides a process for preparing crystal form A, comprising adding the compound of formula (I) to an organic solvent, heating to 30° C. to the reflux temperature to dissolve, and then cooling to 0 to 20° C. within 0.5 to 10 hours to precipitate the crystal.

In some embodiments of the present invention, the above organic solvent is selected from the group consisting of dichloroethane, a $C_{1-6}$ alkyl alcohol, a $C_{4-10}$ ether or cyclic ether, a $C_{2-6}$ ketone, a $C_{2-6}$ ester, benzene optionally substituted by methyl or ethyl or halogen atom(s), wherein the number of the substituent(s) is selected from 1, 2 and/or 3.

In some embodiments of the present invention, the organic solvent is selected from the group consisting of dichloromethane, methanol, ethanol, isopropanol, tetrahydrofuran, dioxane, 2-methyltetrahydrofuran, acetone, ethyl acetate, isopropyl acetate, toluene, xylene and/or chlorobenzene.

The present invention provides a process for preparing crystal form B, comprising adding the compound of formula (I) to a polar organic solvent, and then slowly dropping water to precipitate the crystal.

In some embodiments of the present invention, the above polar organic solvent is selected from the group consisting of a $C_{1-6}$ alkyl alcohol, a $C_{4-10}$ ether or cyclic ether and a $C_{2-6}$ ketone.

In some embodiments of the present invention, the above polar organic solvent is selected from the group consisting of methanol, ethanol, isopropanol, tetrahydrofuran, 2-methyltetrahydrofuran, dioxane and acetone.

The present invention also provides a pharmaceutical composition comprising a therapeutically effective amount of the above compound or the above crystal form as an active ingredient and a pharmaceutically acceptable carrier.

The present invention also provides a use of the above crystal form in manufacturing a medicament for the treatment of respiratory virus infection.

The present invention also provides a use of the above pharmaceutical composition in manufacturing a medicament for the treatment of respiratory virus infection.

DETAILED DESCRIPTION OF THE INVENTION

Figure 1:
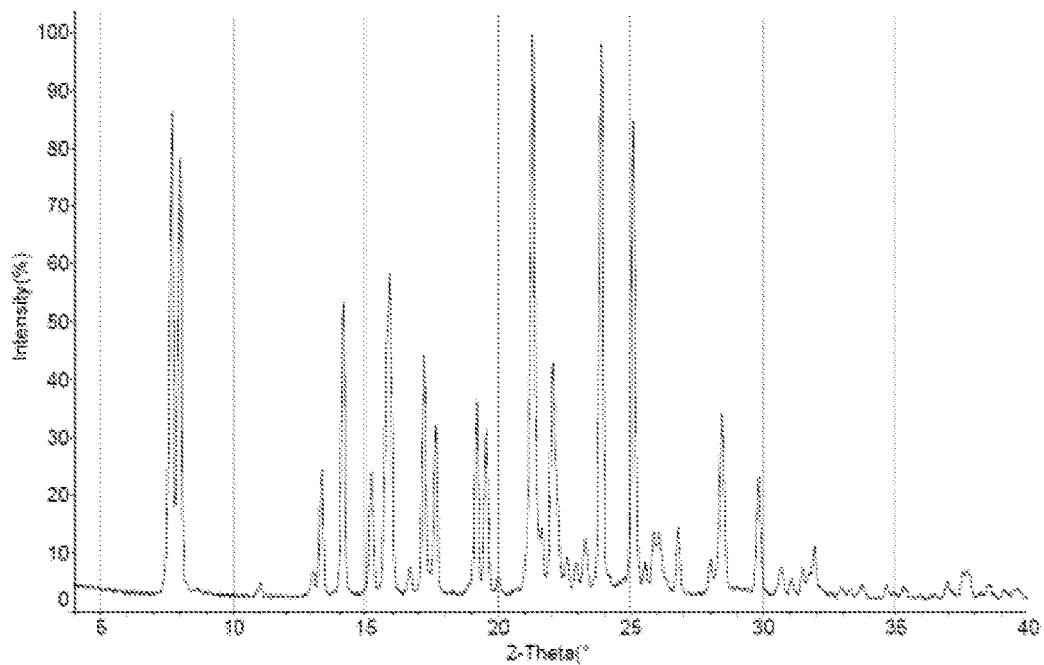
FIG. 1 is a Cu-Kα radiation XRPD spectrum of the crystal form A of the compound of formula (I).
Figure 2:
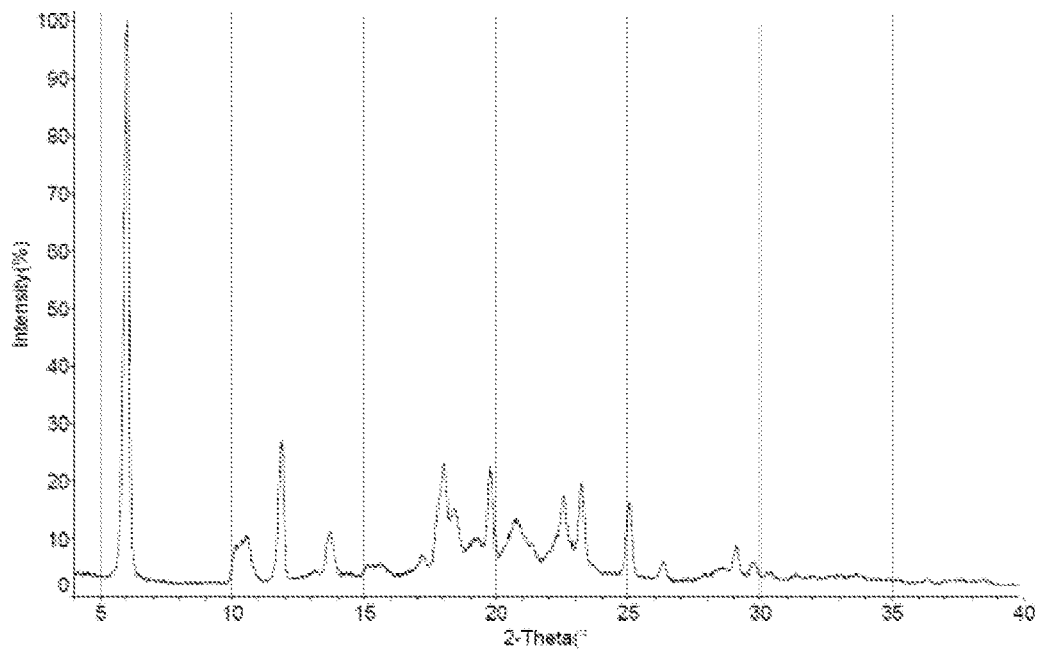
FIG. 2 is a Cu-Kα radiation XRPD spectrum of the crystal form B of the compound of formula (I).

The compound of formula (V) is an important fragment for the compound of formula (I), the reaction operation and post-treatment of preparing the compound of formula (V) from the compound of formula (IV) are simple and the purity of the product is high, the compound of formula (II) precipitates a solid in an inert solvent, and the post-treatment is simple.

The crystal form A and crystal form B of the compound of formula (I) have good stability and good application prospect.

Definitions and Descriptions

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available. The commercially available compounds are named in accordance with suppliers' catalogue. When the mixed solvent is added to the reaction solution, each of the solvents may be mixed first, and then added to the reaction solution, or each of the solvents is added sequentially to the reaction solution and mixed in the reaction system.

The X-Ray Powder Diffraction method is as follows:
Instrument: Bruker D8 ADVANCE X-Ray diffractometer; Target: Cu: K-Alpha; Wavelength λ=1.54179 Å; Tube Voltage: 40 kV; Tube Current: 40 mA; Scanning scope: 4-40°; Sample Rotation speed: 15 rpm; Scanning speed: 10°/min.

The Thermo Gravimetric Analysis (TGA) method of the present invention:
Instrument: TA Q5000 Thermo Gravimetric Analyzer;
Methods: Approximately 2-5 mg of the sample is weighed and placed in a TGA Platinum pot for testing. The method is: room temperature-300° C., the heating rate is 10° C./min.

The Differential Scanning Calorimetry (DSC) method of the present invention:
Instrument: TA Q2000 Differential Scanning Calorimeter;
Methods: Approximately 1 mg of sample is precisely weighed and placed in a DSC aluminum pot for testing, the method is: the temperature is 25° C. to 300° C., and the heating rate is 10° C./min.

The following examples further illustrate the present invention, but it does not mean any unfavorable limitation to the present invention. Herein, the present invention has been described in details, the embodiments of which have been disclosed as well. It is obvious for the person skilled in the art to vary and improve the embodiments of the present invention in the case of not departing from the spirit and scope of the present invention.

Preparation of Compounds of Formula (I)

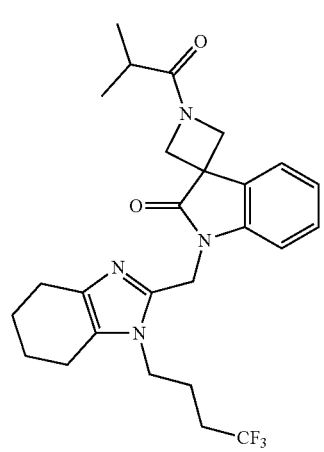

(I)

1-Isobutyryl-1'-((1-(4,4,4-trifluorobutyl)-4,5,6,7-tetrahydro-1H-benzo[d]imidazol-2-yl)methyl)spiro[azetidine-3,3'-indolin]-2'-one

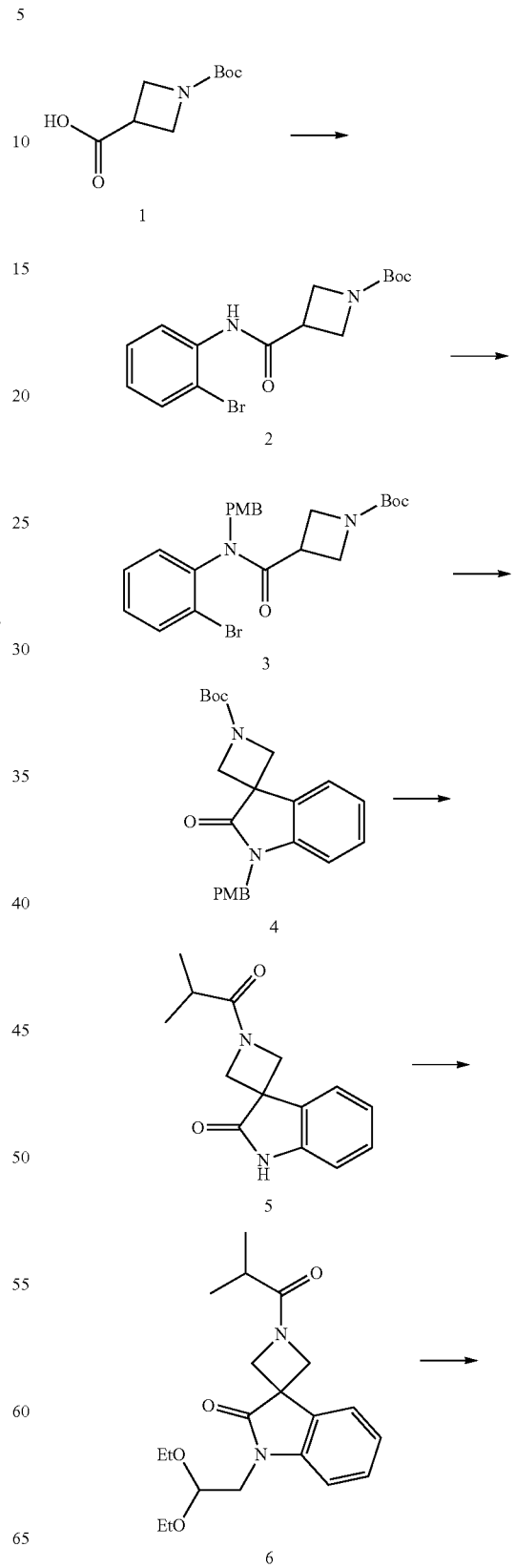

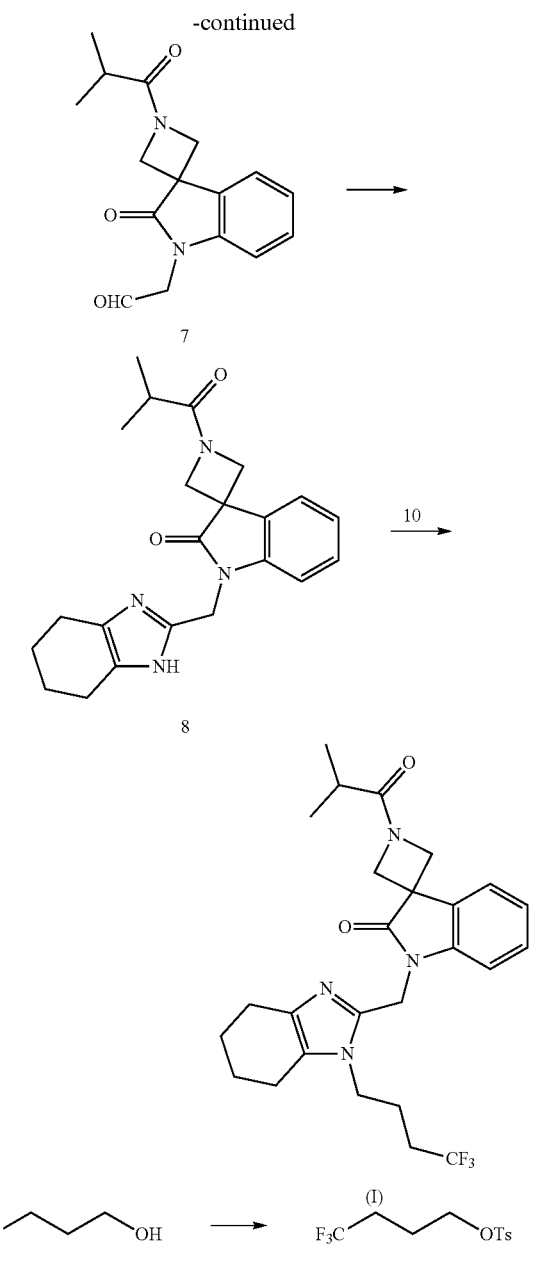

Step 1 tert-Butyl 3-((2-bromophenyl)carbamoyl)azetidine-1-carboxylate 1-(tert-Butoxycarbonyl)azetidine-3-carboxylic acid 1 (3.67 kg, 21.33 mol) and 2-bromoaniline (4.72 kg, 23.25 mol) were added to a 30 L reaction kettle and 7.4 L of ethyl acetate, triethylamine (4.46 L, 32.0 mol) were added. The temperature was cooled to 0-10° C., propylphosphonic acid anhydride (T3P, 50 wt. % solution in ethyl acetate, 15.23 L, 25.6 mol), the temperature was controlled below 35° C. After the addition was complete, the mixture was stirred at room temperature 28-32° C. for 16 hours. The ratio of 1/2 was 0.3% by HPLC detection, the reaction was terminated. The temperature was controlled below 35° C., 5 liters of 5 mol/L aqueous sodium hydroxide solution was slowly added dropwise and the reaction was quenched. The reaction solution was transferred to a 50 L kettle and 7 liters of 5 mol/L aqueous sodium hydroxide solution was added, the pH of the aqueous phase was 7-8 by detection, the mixture was allowed to stand and separate into layers. 5 Liters of 5 mol/L aqueous sodium hydroxide solution was added to the organic layer, and the pH of the aqueous phase was 8-9 by detection, the mixture was allowed to stand and separate into layers. 500 g of sodium hydroxide solids was added to the aqueous layer and the pH of the aqueous phase was 9 to 10 by detection. The mixture was extracted with 5 liters of ethyl acetate. The organic layers were combined and 8 liters of 8 mol/L hydrochloric acid was slowly added with stirring. The pH of the aqueous phase was 6-7 by detection, the mixture was allowed to stand and separate into layers. 8 Liters of 0.3 mol/L hydrochloric acid was added to the organic layer with stirring and the mixture was allowed to stand and separate into layers. 10 Liters of saturated sodium chloride was added to the organic layer and stirred to separate the layers. 10 Liters of saturated sodium chloride was added to the organic layer and stirred to separate the layers. The organic layer was concentrated to 2 liters under reduced pressure and concentrated to dryness by the addition of 5 liters of n-heptane to deliver tert-butyl 3-((2-bromophenyl)carbamoyl)azetidine-1-carboxylate 2 (7.35 kg crude, pale yellow solid), which was used directly in the next step without purification.

MS m/z (ESI): 355.1 [M+1].

$^1$H NMR (400 MHz, CDCl$_3$), δ 8.35 (d, J=7.9 Hz, 1H), 7.66 (br. s., 1H), 7.55 (d, J=7.9 Hz, 1H), 7.34 (t, J=7.7 Hz, 1H), 7.02 (t, J=7.5 Hz, 1H), 4.29-4.14 (m, 4H), 3.46-3.34 (m, 1H), 1.46 (s, 9H).

Step 2 tert-Butyl 3-((2-bromophenyl)(4-methoxybenzyl)carbamoyl)azetidine-1-carboxylate tert-Butyl 3-((2-bromophenyl)carbamoyl)azetidine-1-carboxylate 2 (7.0 kg, 19.71 mol) was added to a 30 L reaction kettle, 14.0 liters of DMF, cesium carbonate (7.7 kg, 23.65 mol) were added. The temperature was controlled below 60° C., and p-methoxybenzyl chloride (3.24 kg, 20.69 mol) was added dropwise. After the addition was complete, the temperature of the reaction was controlled to 98-102° C. and the reaction was carried out for 17 hours. The raw materials were reacted completely by TLC detection. The reaction solution was transferred to a 50 L kettle, 15 liters of ethyl acetate and 10 liters of water were added, and the mixture was stirred for 10 minutes and allowed to stand and separate into layers. The aqueous layer was extracted with 15 liters of ethyl acetate. The organic layers were combined and washed with 10 liters of water and 10 liters of 15% brine, respectively. The organic layer was concentrated to dryness under reduced pressure, and 20 liters of n-heptane was added and the mixture was triturated for 3 hours, and the filter cake was dried in vacuo to deliver tert-butyl 3-((2-bromophenyl)(4-methoxybenzyl)carbamoyl)azetidine-1-carboxylate 3 (8.78 kg, white solid), which was used directly in the next step without purification.

MS m/z (ESI): 475.2 [M+1].

$^1$H NMR (400 MHz, CDCl$_3$) δ 7.69 (dd, J=1.9, 7.7 Hz, 1H), 7.25-7.16 (m, 2H), 7.10 (d, J=8.5 Hz, 2H), 6.79 (d, J=8.8 Hz, 2H), 6.65 (dd, J=2.0, 7.3 Hz, 1H), 5.56 (d, J=14.1

Hz, 1H), 4.29 (br. s., 1H), 4.00 (d, J=14.3 Hz, 2H), 3.79 (s, 3H), 3.72 (br. s., 1H), 3.56 (br. s., 1H), 3.10-3.01 (m, 1H), 1.41 (s, 9H).

Step 3 tert-Butyl 1'-(4-methoxybenzyl)-2'-oxospiro[azetidine-3,3'-indoline]-1-carboxylate tert-Butyl 3-((2-bromophenyl)(4-methoxybenzyl)carbamoyl)azetidine-1-carboxylate 3 (3.0 kg, 6.31 mol) was added to a 30 L reaction kettle, 12 liters of 1,4-dioxane was added and sodium tert-butoxide (0.91 kg, 9.47 mol) was added. The reaction kettle was sealed, vacuumed for 5 minutes, filled with nitrogen, which were repeated 3 times. The exhaust port of the reaction kettle was liquid sealed, and palladium acetate (70.84 g, 0.32 mol), tricyclohexylphosphine (176.97 g, 0.63 mol) were added under continuous nitrogen flow. The nitrogen was kept filled, and the outside temperature of the reaction kettle was set at 75° C. When the internal temperature rose to 60° C., the internal wall of the reaction kettle began to condense which was lasted for 10 minutes. At this time the internal temperature is 65° C. When the outside temperature of the reaction kettle was set at 90° C., the internal temperature slowly rose to 78° C., the color of the reaction solution gradually changed from dark brown to dark gray, while the condensation of the inner wall of the reaction kettle was aggravated and the temperature rise was accelerated. At the same time, the nitrogen inlet rate was increased, and the exhaust port of the reaction kettle at the liquid seal was opened. The internal temperature continued to rise to 103° C. and began to cool after 103° C. for 10 minutes. The nitrogen inlet speed was slowed down, and the reaction system was liquid sealed, the internal temperature gradually reduced to 90° C. The reaction was continued at 90° C. for 0.5 hour. Sample was taken and monitored, HPLC showed that 3 completely disappeared, a by-product about 10% appeared. The reaction kettle was cooled to room temperature, 10 liters of ethyl acetate was added, 15 liters of water was added and stirred for 5 minutes, the mixture was allowed to stand and separate into layers. The aqueous layer was extracted with 10 liters of ethyl acetate and the organic layers were combined. The organic layer was washed once with 10 liters of 15% brine, after separation, the mixture was concentrated under reduced pressure to 10 liters of solvent, and 5 liters of n-heptane was added, and the mixture was concentrated to dryness to give a 3 kg of wet weight crude. The wet weight crude was transferred to a reaction kettle, 9 liters of ethyl acetate, 0.3 kg of 1,3,5-triazine-2,4,6-trithiol trisodium salt monohydrate were added, and the mixture was heated to 80° C. and stirred for 2 hours and then the hot mixture was filtered. The filtrate was concentrated to dryness under reduced pressure to give a 2.8 kg of crude product. The crude product was transferred to a reaction kettle, 1.125 liters of ethyl acetate was added, and the mixture was heated to 80° C. and stirred for 1 hour. 4.5 Liters of n-heptane was added slowly. After the addition was complete, the mixture was stirred at 80° C. for 1 hour. The mixture was cooled to 60° C. and maintained at 60° C. for 1 hour. The reaction kettle was set to cool to 20° C. within 7 hours, and the mixture was stirred at 20° C. for 8 hours. The mixture was filtered to deliver a filter cake tert-butyl 1'-(4-methoxybenzyl)-2'-oxospiro[azetidine-3,3'-indoline]-1-carboxylate 4 (1.9 kg, light brown solid), which was used directly in the next step without purification.

MS m/z (ESI): 395.2 [M+1].
$^1$H NMR (400 MHz, CDCl$_3$) δ 7.59 (d, J=7.3 Hz, 1H), 7.32-7.26 (m, 3H), 7.15 (t, J=8.0 Hz, 1H), 6.89 (d, J=8.5 Hz, 2H), 6.82 (d, J=7.8 Hz, 1H), 4.89 (s, 2H), 4.47 (d, J=8.3 Hz, 2H), 4.13 (d, J=8.0 Hz, 2H), 3.82 (s, 3H), 1.55 (s, 9H).

Step 4

1-Isobutyrylspiro[azetidine-3,3'-indolin]-2'-one 3.3 Liters of anisole was added to a 30 L reaction kettle, tert-butyl 1'-(4-methoxybenzyl)-2'-oxospiro[azetidine-3,3'-indoline]-1-carboxylate 4 (3.3 kg, 8.37 mol) was added. The temperature was controlled not higher than 15° C., and 6.6 liters of trifluoroacetic acid was added. After the addition was complete, the reaction was maintained at 15° C. and reacted for 0.5 h. The temperature was controlled not higher than 15° C., and 2.22 liters of trifluoromethanesulfonic acid was added dropwise. After the addition was complete, the mixture was maintained at 15° C. and stirred for 14 hours. The temperature was controlled not higher than 15° C., 6.6 liters of ethyl acetate was added to the reaction kettle, and the mixture was stirred for 0.25 hour. The reaction solution was transferred to a 50 L kettle and 12 liters of n-heptane was added dropwise to the 50 L kettle to precipitate a solid, the mixture was continued to stir for 0.5 hour. The mixture was filtered, and the filter cake weighed 4.0 kg. The filter cake was transferred to a 30 L reaction kettle, 13.2 liters of dichloromethane was added, the temperature was controlled not higher than 15° C. and triethylamine (4.08 L, 29.28 mol) was added, the temperature was controlled not higher than 5° C., and isobutyryl chloride (0.865 L, 8.37 mol) diluted with 0.8 liter of dichloromethane was added dropwise within about 2 hours. After the addition was complete, the temperature was maintained at 5° C. for 0.25 hour. The purity of the main product was 91.5% by HPLC detection. The temperature was not higher than 15° C., 0.13 liters of methanol was added and the mixture was stirred for 0.25 hour. The temperature was controlled not higher than 15° C., 5 liters of 2 mol/L hydrochloric acid was added. The pH of the aqueous phase was about 3 by detection. The mixture was allowed to stand and separate into layers, the aqueous layer was extracted four times with 3 liters of dichloromethane/methanol (v/v=10/1). The organic layers were combined and washed with 5 liters of water. The organic layer was concentrated to 1.5 liters under reduced pressure, 10 liters of ethyl acetate was added and the mixture was concentrated to 4 liters, and then the concentrate was transferred to a 30 L reaction kettle, heated to 70° C., and 4 liters of n-heptane was added. The temperature of the reaction kettle was controlled at 70° C. and stirred for 6 hours. The temperature was cooled to 5° C. within 10 hours, and the mixture was continued to stir at 5° C. for 50 hours. The mixture was filtered to give a 2.6 kg solid. The solid contained triethylammonium trifluoromethanesulfonate by $^1$H NMR detection. The solid was transferred to a 30 L reaction kettle, 7.5 liters of distilled water was added, the mixture was stirred for 16 hours, and filtered to give a 2.95 kg wet weight powder, which was dried at 50° C. for 48 hours in vacuo to deliver 1-isobutyrylspiro[azetidine-3,3'-indolin]-2'-one 5 (1.54 kg, pale yellow solid, HPLC purity 99%).

MS m/z (ESI): 245.2 [M+1].
$^1$H NMR (400 MHz, CDCl$_3$) δ9.03 (br. s., 1H), 7.48 (d, J=7.5 Hz, 1H), 732-7.23 (m, 1H), 7.16-7.05 (m, 1H), 6.96 (d, J=8.0 Hz, 1H), 4.59 (d, J=8.0 Hz, 1H), 4.44 (d, J=9.5 Hz,

1H), 4.30 (d, J=8.0 Hz, 1H), 4.19 (d, J=9.5 Hz, 1H), 2.53 (td, J=6.8, 13.6 Hz, 1H), 1.19 (dd, J=2.5, 6.5 Hz, 6H).

Step 5

1'-(2,2-Diethoxyethyl)-1-isobutyrylspiro[azetidine-3,3'-indolin]-2'-one

15 Liters of DMF was added to a 30 L reaction kettle, 1-isobutyrylspiro[azetidine-3,3'-indolin]-2'-one 5 (2.94 kg, 11.35 mol), cesium carbonate (5.55 kg, 17.02 mol), 2-bromo-1,1-diethoxyethane (2.50 kg, 12.48 mol) were added. The temperature was controlled at 88-92° C. and reacted for 18 hours.

Sample was taken and detected by HPLC, the ratio of 5/6 was 0.7%, the reaction was complete. The temperature was cooled to 20° C., the total volume of the reaction mixture was about 20 liters. The reaction solution was transferred to two 50 liter kettles, 10 liters per kettle. 12 Liters of ethyl acetate, 28 liters of water, was added respectively to the 50 liter reaction kettle, and the mixture was stirred for 5 mixtures, and allowed to stand and separate into layers. The aqueous layer was extracted twice with ethyl acetate, and 7 liters each time. The organic layers were combined, washed twice with 10% brine, 5 liters each time, and washed again with 5 liters of water. All organic layers were combined and then concentrated to 7 liters at 45° C. under reduced pressure, 7 liters of dichloromethane was added, concentrated to 4 liters at 45° C., 4 liters of dichloromethane was added and concentrated to dryness under reduced pressure at 45° C. to deliver 1'-(2,2-diethoxyethyl)-1-isobutyrylspiro[azetidine-3,3'-indolin]-2'-one 6 (4.17 kg, bright yellow oil, HPLC purity 93.9%, nuclear magnetic weight content 91.0%).

MS m/z (ESI): 361.2 [M+1]
$^1$H NMR (400 MHz, CDCl$_3$) δ 7.46 (d, J=7.3 Hz, 1H), 7.30 (dt, J=1.0, 7.8 Hz, 1H), 7.16-7.08 (m, 1H), 7.05 (d, J=8.0 Hz, 1H), 4.69 (t, J=5.3 Hz, 1H), 4.56 (d, J=8.0 Hz, 1H), 4.40 (d, J=9.3 Hz, 1H), 4.26 (d, J=8.0 Hz, 1H), 4.15 (d, J=9.3 Hz, 1H), 3.88-3.78 (m, 2H), 3.78-3.69 (m, 2H), 3.55-3.45 (m, 2H), 2.51 (td, J=6.8, 13.7 Hz, 1H), 1.19-1.10 (m, 12H).

Step 6

2-(1-Isobutyryl-2'-oxospiro[azetidine-3,3'-indolin]-1'-yl)acetaldehyde

1'-(2,2-Diethoxyethyl)-1-isobutyrylspiro[azetidine-3,3'-indolin]-2'-one 6 (4.16 kg, 10.5 mol) was dissolved in 6.24 liters of dichloromethane and added to a 30 liters reaction kettle and 2.08 liters of water was added. The temperature was controlled at 0-5° C., 6.24 liters of trifluoroacetic acid was added. After the addition was complete, the reaction was carried out at 28-32° C. for 3 hours. Sample was taken and detected by HPLC, the ratio of 6/7 was 0.95%, and the reaction was complete. The reaction mixture was cooled to 15° C., and the total volume of the reaction solution was 18 liters. 12 Liters of dichloromethane was added, and the total volume was 30 liters, which was transferred to two 50 liter kettles, 15 liters per kettle. 30 Liters of water was added to the 50 liters kettle, respectively and the mixture was stirred for 10 minutes and allowed to stand and separate into layers. The aqueous layer was extracted once with 10 liters of dichloromethane, the organic layers were combined and washed with 10% brine for three times, 8 liters each time, the organic layer was washed once with 8 liters saturated sodium bicarbonate and 8 liters water. The 10% brine, the saturated sodium bicarbonate and the aqueous layer after washing were combined and extracted with 10 liters of dichloromethane. All the extracted organic layers were combined, concentrated to 5 liters under reduced pressure at 35° C., and concentrated to dryness by the addition of 5 L of ethyl acetate to deliver 2-(1-isobutyryl-2'-oxospiro[azetidine-3,3'-indolin]-1'-yl)acetaldehyde 7 (3.41 kg, crude yellow oil), which was used directly in the next step without purification.

MS m/z (ESI): 287.1 [M+1].
$^1$H NMR (400 MHz, CDCl$_3$) δ 9.70 (s, 1H), 7.54 (d, J=7.0 Hz, 1H), 7.32 (dt, J=1.0, 7.8 Hz, 1H), 7.22-7.16 (m, 1H), 6.67 (d, J=7.8 Hz, 1H), 4.66-4.49 (m, 3H), 4.44 (d, J=9.5 Hz, 1H), 4.33 (d, J=8.0 Hz, 1H), 4.21 (d, J=9.5 Hz, 1H), 2.53 (quin, J=6.8 Hz, 1H), 1.18 (dd, J=3.5, 6.8 Hz, 6H).

Step 7

1-Isobutyryl-1'-((4,5,6,7-tetrahydro-1H-benzo[d]imidazol-2-yl)methyl)spiro[azetidine-3,3'-indolin]-2'-one 2-(1-Isobutyryl-2'-oxospiro[azetidine-3,3'-indolin]-1'-yl)acetaldehyde 7 (3.4 kg, crude) was dissolved in 17 liters of DMF and added to a 30 liters reaction kettle, 1,2-cyclohexanedione (1.34 kg, 11.96 mol), ammonium acetate (3.84 kg, 49.81 mol) were added, and the mixture was reacted at 68-72° C. for 2 hours. Sample was taken and detected by HPLC, and the reaction was complete. The reaction mixture was cooled to 15° C., and the total volume of the reaction solution was 20 liters, which was transferred to two 50 liter kettles, 10 liters per kettle. 9 Liters of dichloromethane, 4.5 liters of ethyl acetate, 17 liters of 1.5 mol/L sodium hydroxide, 17 liters of 10% brine were added to the 50 liter kettle, respectively, and the mixture was stirred for 10 minutes, and allowed to stand and separate into layers. The organic layer was washed for three times with 10% brine, 9 liters each time and washed with 9 liters of water again. All the extracted organic layers were combined, concentrated to 10 liters at 40° C. under reduced pressure, and 17 liters of ethyl acetate was added and the mixture was concentrated to dryness at 40° C. under reduced pressure to give a crude product. The crude product was transferred to a 30 L reaction kettle and 13 liters of ethyl acetate was added and the mixture was stirred at 70° C. for 1 hour. 13 Liters of n-heptane was added and the mixture was stirred at 70° C. for 1 hour. The temperature was controlled to cool from 70° C. to 0° C. in 2 hours and the mixture was stirred at 0° C. for 1 hour. The mixture was filtered and the filter cake was dried in vacuum at 60° C. for 18 hours to deliver 1-isobutyryl-1'-((4,5,6,7-tetrahydro-1H-benzo[d]imidazol-2-yl)methyl)spiro[azetidine-3,3'-indolin]-2'-one 8 (3.3 kg, pale yellow solid, HPLC purity 95.9%, nuclear magnetic content 93.6%).

MS m/z (ESI): 379.2 [M+1]
$^1$H NMR (400 MHz, CDCl$_3$) δ 9.62 (br. s., 1H), 7.46 (d, J=7.3 Hz, 1H), 7.36-7.28 (m, 1H), 7.20 (d, J=7.8 Hz, 1H), 7.17-7.10 (m, 1H), 4.94-4.79 (m, 2H), 4.54 (d, J=8.0 Hz, 1H), 4.38 (d, J=9.3 Hz, 1H), 4.26 (d, J=8.0 Hz, 1H), 4.13 (d, J=9.5 Hz, 1H), 2.50 (d, J=6.8 Hz, 4H), 1.75 (br. s., 4H), 1.17 (d, J=6.8 Hz, 6H).

Step 8

4,4,4-Trifluorobutyl 4-methylbenzenesulfonate 4,4,4-Trifluorobutan-1-ol 9 (1.5 kg, 11.71 mol) was dissolved in 7.5 liters of tetrahydrofuran and added to a 30 L reaction kettle. A 20% potassium hydroxide solution (1.97 kg, 7.5 L) was slowly added dropwise at 0-5° C. After the addition was complete, p-toluenesulfonyl chloride (3.35 kg, 17.57 mol) was added in batches at 0-5° C. After the addition was complete and the mixture was reacted at 10° C. for 2 hours. The reaction was complete by TLC detection. 4.5 Liters of ethyl acetate, 4.5 liters of water were added and the mixture was stir for 5 minutes and allowed to stand and separate into layers. The aqueous layer was extracted twice with ethyl acetate and 4.5 liters each time. The organic layer was concentrated under reduced pressure to deliver 4,4,4-trifluorobutyl 4-methylbenzenesulfonate 10 (2.95 kg, colorless oil).

$^1$H NMR (400 MHz, CDCl$_3$) δ 7.77 (d, J=8.0 Hz, 2H), 7.35 (d, J=8.0 Hz, 2H), 4.07 (t, J=6.0 Hz, 2H), 2.45 (s, 3H), 2.21-2.12 (m, 2H), 1.93-1.89 (m, 2H).

Step 9

1-Isobutyryl-1'-((1-(4,4,4-trifluorobutyl)-4,5,6,7-tetrahydro-1H-benzo[d]imidazol-2-yl)methyl)spiro[azetidine-3,3'-indolin]-2'-one (I)

12 Liters of DMF was added to a 30 L reaction kettle, 1-isobutyryl-1'-((4,5,6,7-tetrahydro-1H-benzo[d]imidazol-2-yl)methyl)spiro[azetidine-3,3'-indolin]-2'-one 8 (3.2 kg, 8.81 mol), cesium carbonate (3.87 kg, 11.87 mol), 4,4,4-trifluorobutyl-4-methylbenzenesulfonate 10 (2.51 kg, 8.86 mol) were added, and the mixture was reacted at 88-92° C. for 3.5 hours. Sample was taken and detected by HPLC, the ratio of 10/8 was 0%, and the reaction was complete. The reaction mixture was cooled to 15° C., and the total volume of the reaction solution was 18 liters, which was transferred to two 50 liter kettles, 9 liters per kettle. 12 Liters of ethyl acetate, 24 liters of distilled water were added to the 50 liters kettle, respectively and the mixture was stirred for 10 minutes and allowed to stand and separate into layers. The aqueous layer was extracted with 12 liters of ethyl acetate again and the organic layers were combined. The organic layer was washed for three times with distilled water, 8 liters each time. All the extracted organic layers were combined and concentrated to dryness at 45° C. under reduced pressure, and dried in vacuo to give 3.8 kg of crude product, HPLC purity 93.5%. 2.8 kg Of the crude product was taken and added to a 30 L reaction kettle, 1.68 liters of ethanol was added, and the mixture was heated to 65° C. to dissolve completely. 3.36 Liters of n-heptane was added and the mixture was continued to stir at 65° C. for 10 minutes. The hot mixture was filtered, the filter cloth bag was washed with 1.26 liters of ethanol/n-heptane (v/v=1/2), which was combined into the mother liquor. The mother liquor was transferred to a 30 L reaction kettle, heated to 75° C., 8.4 liters of n-heptane was added and the mixture was continued to stir for 10 minutes. The mixture was cooled to 55-57° C., 3 g of seed crystal was added and the mixture was continued to stir for 1 hour at 55-57° C. The temperature of the mixture was cooled to 2-4° C. in 4 hours and maintained at 2-4° C. and stirred for 16 hours. The mixture was filtered and the filter cake was rinsed with 2.8 liters of ethanol/n-heptane (v/v=1/6) and dried in vacuum at 45° C. for 16-24 hours to deliver a pale yellow powder 2.1 kg and the HPLC purity was 98.9%. The powder was pulverized by a jet mill to deliver 1-isobutyryl-1'-((1-(4,4,4-trifluorobutyl)-4,5,6,7-tetrahydro-1H-benzo[d]imidazol-2-yl)methyl)spiro[azetidine-3,3'-indolin]-2'-one (I) (2.05 kg, light yellow white solid, HPLC purity 98.7%, nuclear magnetic weight content 98.2%).

MS m/z (ESI): 489.3 [M+1].

$^1$H NMR (400 MHz, CD$_3$OD) δ 7.61 (d, J=8.03 Hz, 1H), 7.49 (d, J=7.28 Hz, 1H), 7.37 (t, J=7.78 Hz, 1H), 7.21-7.15 (m, 1H), 5.05-4.92 (m, 2H), 4.56 (d, J=8.03 Hz, 1H), 4.41 (d, J=9.29 Hz, 1H), 4.28 (d, J=7.78 Hz, 1H), 4.18 (d, J=9.54 Hz, 1H), 4.10-3.91 (m, 2H), 2.63-2.44 (m, 5H), 2.31-2.05 (m, 2H), 1.81 (br. s., 6H), 1.20 (d, J=6.78 Hz, 6H).

Preparation of Crystal Form A

About 0.6 g of the compound of formula (I) was weighed and added to 5 mL of ethyl acetate, the mixture was heated to 60° C. and stirred to dissolve to make it into a saturated solution. The hot solution was filtered, and the filtrate was naturally cooled to 10 to 15° C. and which was took 1.5 to 2 hours. The precipitated solid was collected by filtration and dried under vacuum at 40° C. for 20 hours to deliver 0.39 g of solid powder. The result of XRPD detection was crystal form A.

Preparation of Crystal Form B

About 0.25 g of the compound of formula (I) was weighed and 2.5 mL of tetrahydrofuran was added at room temperature 10-15° C. to form a saturated solution. The solution was filtered and the anti-solvent deionized water was gradually added dropwise to 6 mL to gradually precipitate the milky white solid. The mixture was continued to stir for 16 to 20 hours. The precipitated solid was collected by filtration and dried under vacuum at 40° C. for 20 hours to deliver 0.13 g of solid powder. The result of XRPD detection was crystal form B.

The Stability Experiment of Crystal Form a of the Compound of Formula (I) in Different Solvents.

A plurality of 50 mg of crystal form A of the compound of formula (I) were weighed in parallel, 0.2 to 0.3 mL of the single or mixed solvent in the table below was added, respectively. The mixture was stirred at 40° C. If the compound was completely dissolved, the sample was allowed to cool to room temperature, and if the solid was precipitated, the mixture was continued to stir; and if the sample remained in solution, the solvent was naturally evaporated to remove. After all the suspensions were stirred for 2 days, the solids in all samples were collected and XRPD was used to detect the crystal form state. The results were shown in Table 3.

TABLE 3

The Stability Experiment of Crystal Form A in Different Solvents

| No. | Solvent | Appearance (2 days) | Result |
|---|---|---|---|
| 1 | Ethanol | The solid was precipitated after the solvent was naturally evaporated to remove. | Crystal Form A |
| 2 | Acetone | The solid was precipitated after the sample was cooled to room temperature. | Crystal Form A |
| 3 | Ethyl acetate | Suspension | Crystal Form A |
| 4 | 2-Methyltetrahydrofuran | Suspension | Crystal Form A |
| 5 | Toluene | Suspension | Crystal Form A |
| 6 | Dioxane | Suspension | Crystal Form A |

TABLE 3-continued

The Stability Experiment of Crystal Form A in Different Solvents

| No. | Solvent | Appearance (2 days) | Result |
|---|---|---|---|
| 7 | Methanol:water = 3:1 | The solid was precipitated after the sample was cooled to room temperature. | Crystal Form A |
| 8 | Ethanol:water = 3:1 | Suspension | Crystal Form B |
| 9 | Acetone:water = 1:2 | Suspension | Crystal Form B |

The Solid Physical Stability Experiment of Crystal Form A of the Compound of Formula (I) Under Different Temperature and Humidity Conditions.

3 Parts of crystal form A of the compound of formula (I) solid were weighed in parallel, each about 50 mg, and then placed in the bottom of the glass vials, spread out to form a thin layer, the bottlenecks were sealed with aluminum foil, and some small holes were made in the aluminum foil to ensure that the sample can be fully in contact with the ambient air. The three prepared samples were placed at 25° C./92.5% relative humidity, 60° C. and 60° C./75% relative humidity, respectively, and the physical stability of the samples were observed for 10 days. At the same time, crystal form A of the compound of formula (I) solid about 50 mg was weighed separately, placed in the bottom of a glass vial, sealed with a threaded-cap and stored at −20° C. as a control sample. On the tenth day, all samples were removed and returned to room temperature. The appearance changes of samples were observed, and the crystal form of samples was detected by XRPD. The solid physical stability of the crystal form A of the compound of formula (I) was determined by comparing the accelerated sample with the control sample. The experimental results for the solid physical stability of crystal form A were shown in table 4 below.

TABLE 4

The Solid Physical Stability Experiment of Crystal Form A under Different Temperature and Humidity Conditions

Figure 3:
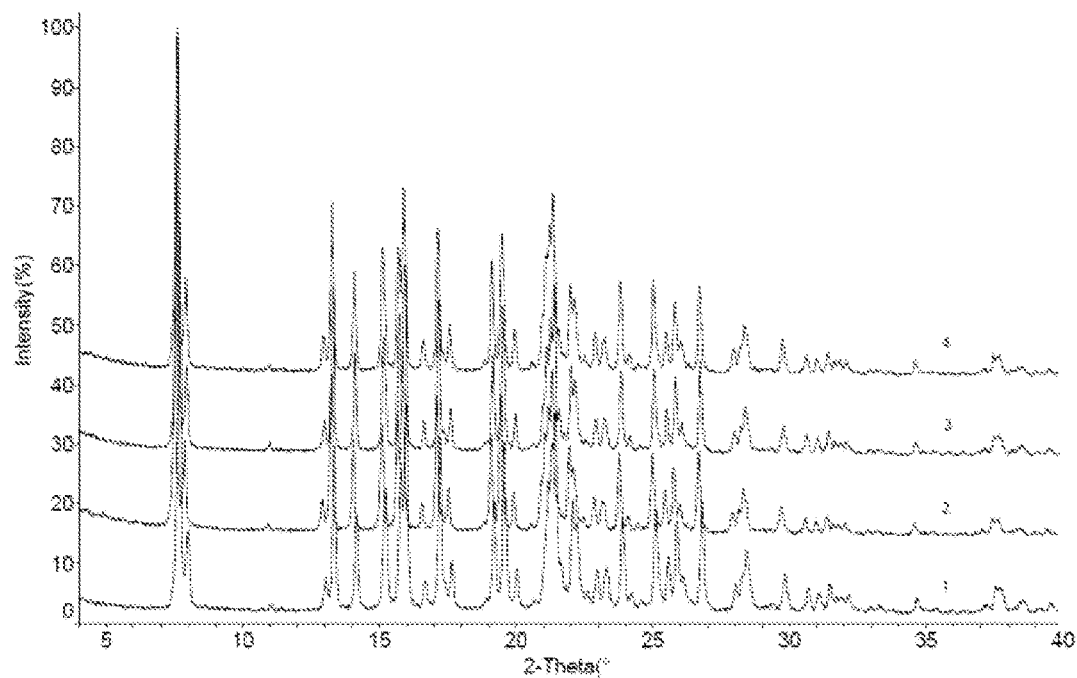
FIG. 3 is a Cu-Kα radiation XRPD spectrum of the crystal form A of the compound of formula (I) at different temperatures and humidity conditions.
Figure 4:
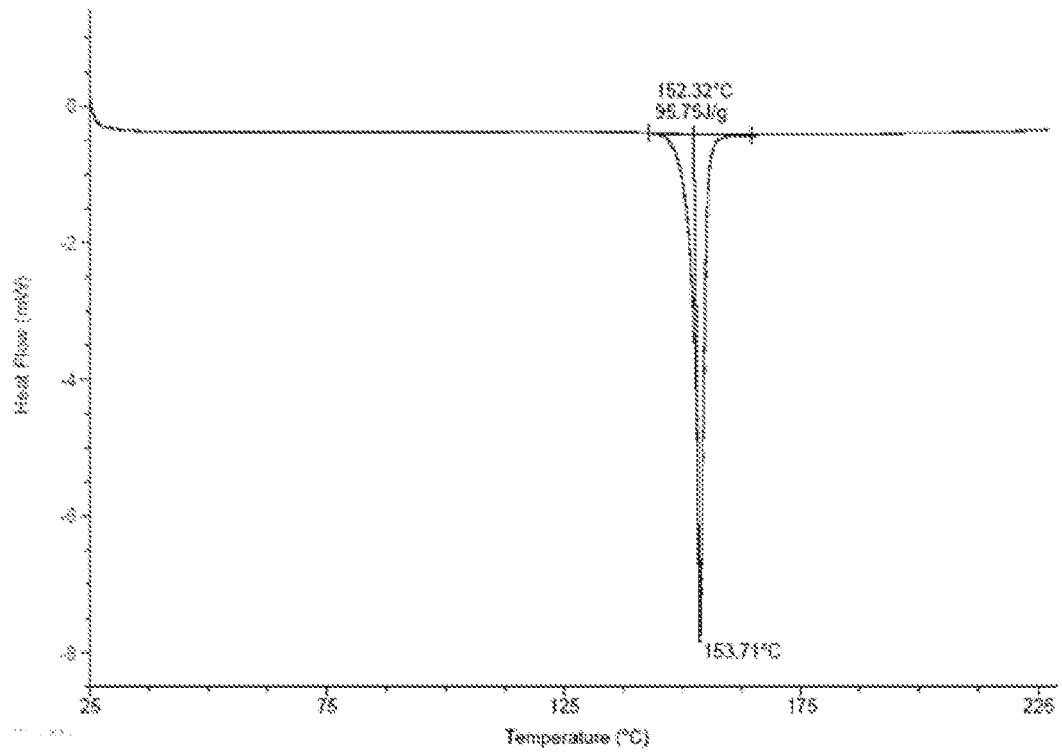
FIG. 4 is a DSC spectrum of the crystal form A of the compound of formula (I).
Figure 5:
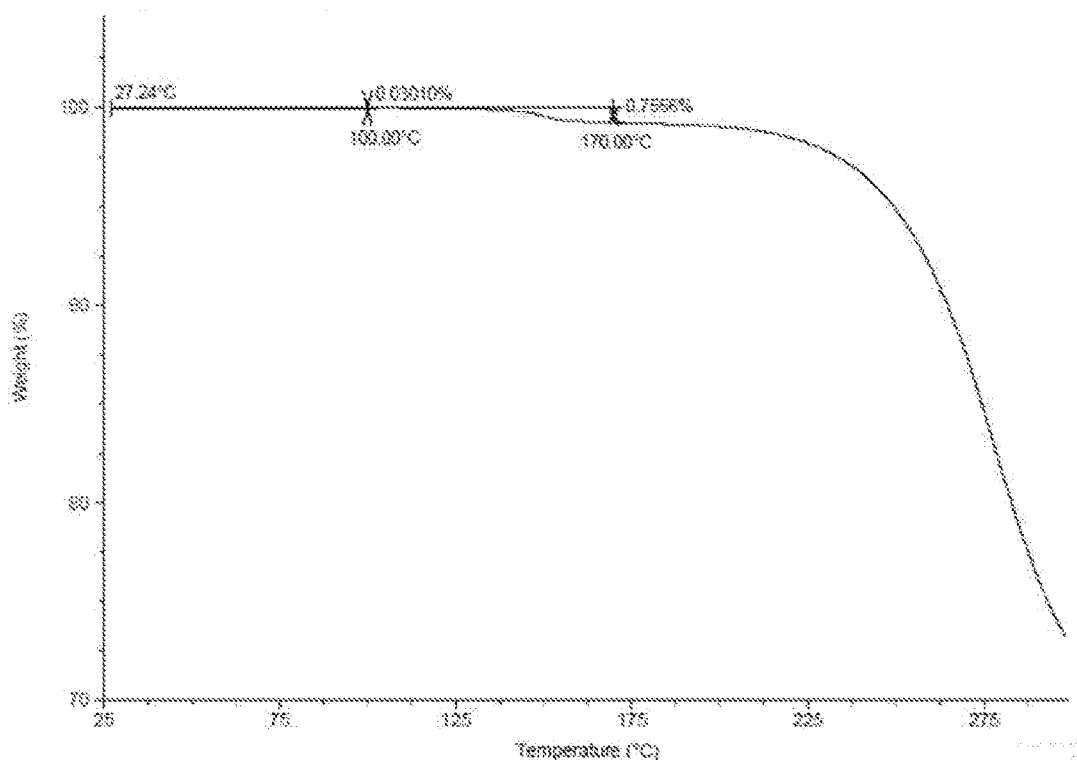
FIG. 5 is a TGA spectrum of the crystal form A of the compound of formula (I).

| Inspection Item | Time Point | 0 day (−20° C. Sealed Storage) (Control Sample) | 25° C./ 92.5% Relative Humidity (Open) | 60° C./75% Relative Humidity (Open) | 60° C. (Open) |
|---|---|---|---|---|---|
| Crystal Form | 10$^{th}$ day | Crystal Form A (FIG. 3 Spectrum 1) | Crystal Form A (FIG. 3 Spectrum 3) | Crystal Form A (FIG. 3 Spectrum 4) | Crystal Form A (FIG. 3 Spectrum 2) |
| Character | 10$^{th}$ day | White Powder | White Powder | White Powder | White Powder |

The approximate solubility test of crystal form A of the compound of formula (I).

At room temperature (20 to 30° C.), 1 to 1.5 mg of crystal form A of the compound of formula (I) was added to a volumetric flask, and a single organic solvent or a mixed solvent was added several times in a small amount until the visual solution was clear or no solid particles present. The approximate solubility of crystal form A in different solvents was determined and the results were shown in Table 5.

TABLE 5

The Solubility of Crystal Form A of the Compound of Formula (I) in Different Solvents

| Solvent | The approximate solubility (mg/mL) | Solvent | The approximate solubility (mg/mL) |
|---|---|---|---|
| Methanol | 115.0-231.0 | Toluene | 28.0-32.5 |
| Ethanol | 42.0-52.5 | n-Heptane | <2 |
| Isopropanol | 13.9-20.9 | Cyclohexane | <2 |
| n-Butyl alcohol | 25.9-29.5 | Dioxane | 45.0-56.5 |
| Acetonitrile | 42.0-53.6 | $H_2O$ | <2 |
| Acetone | 45.9-57.4 | Methanol-$H_2O$ (1:1) | <2 |
| 2-Butanone | 56.9-75.8 | Methanol-$H_2O$ (3:1) | 45.0-56.5 |
| Methyl isobutyl ketone | 22.9-25.5 | Ethanol-$H_2O$ (1:1) | 2.0-2.7 |
| Ethyl acetate | 29.0-34.0 | Ethanol-$H_2O$ (3:1) | 22.0-24.5 |
| Isopropyl acetate | 18.0-20.5 | Acetonitrile-$H_2O$ (1:1) | 46.0-58.0 |
| Methyl tert-butyl ether | 3.0-3.7 | Acetone-$H_2O$ (1:2) | <2 |
| Tetrahydrofuran | 113.0-226.0 | Isopropanol-$H_2O$ (1:1) | 2.5-3.0 |
| 2-Methyltetrahydrofuran | 45.0-56.7 | | |

Embodiment 1 Evaluation In Vitro

RSV long CPE assay

Experimental Purpose:

The $EC_{50}$ and $CC_{50}$ values of anti-RSV respiratory syncytial virus compounds were detected by cytopathology.

Experimental Materials:

Cell Line: Hep2

Virus Strain: RSV aspiration syncytial virus (Along strain)

Cell Culture Medium (DMEM/F12, Gibco #11330, 10% serum Gibco #16140 and 1% penicillin-streptomycin (penicillin 5000 IU/mL, streptomycin 10 mg/mL), Gibco #15140 were added)

Trypsin (Gibco #12605010)

PBS (Thermo #SH30264.01)

Trypan Blue (Cat. Invitrogen #15250061)

CCK-8 (Dojindo #CK04-20)

$CO_2$ Incubator, Thermo 240 I

Multidrop Automatic Dispenser, Thermo

POD 810 Plate Assembler Fully Automatic Microplate Pretreatment System, Labcyte

Scepter Handheld Automated Cell Counter, Millipore

Microplate Spectrophotometer, Molecular Device.

Experimental Procedures and Methods:

a) Cell Inoculation (Hep2 cell)

1) The cell culture medium was removed and washed with 10 mL of PBS;

2) The preheated trypsin was added to the cleaned culture flask and rotating the flask to allow the trypsin to uniformly cover the culture flask. And then sucked it into a 37° C., 5% $CO_2$ incubator to digest.

3) Each T150 was suspended in 10 to 15 mL culture medium, 0.1 mL was taken and then diluted twice with trypan blue solution.

4) The cells were diluted to $5 \times 10^4$/mL with the culture medium and the diluted cells were added to the corning 384 plates (Cat 3701) (30 μL/well, 1500 cells/well) with an automatic dispenser (Thermo Scientific). The cells were centrifuged (300 rpm) and the cells were adhered to the wall and placed in a 37° C., 5% $CO_2$ incubator overnight.

b) Compound addition:

1) The compound dissolved in 100% DMSO was diluted in a half logarithm and added to the cell plate using an Echo liquid handler. To ensure that the final concentration of DMSO was 1%;

| EC$_{50}$ (μM) | CC$_{50}$ (μM) |
|---|---|
| 0.1-0.00014 μM (8 points of a half logarithmic dilution) | 100-0.14 μM (8 points of a half logarithmic dilution) |

2) Cell control well: no compound and virus; virus control well: no compound.

c) Virus Inoculation:

The RSV virus was diluted to 100 TCID50/30 μL with a cell culture medium cultured at 4° C., and the diluted virus was added to the cell plates (30 μL/well) with a Multidrop® automatic dispenser and placed in a 37° C., 5% CO$_2$ incubator for 5 days.

d) Cytopathic Effect Detection:

1) After 5 days, the cytopathic of each well was observed. Under normal circumstances, there was no cytopathy in the cell control wells, the cells in the virus control wells were completely pathologies.

2) CCK-8 (Dojindo-CK04-20, 6 μL/well) was added to 384 well plates with Multidrop® automatic dispenser.

3) The mixture was placed in a 37° C., 5% CO$_2$ incubator for 3 to 4 hours, the absorbance values were read at the wavelength of 450 nm and 630 nm using a microplate reader (SPECTRA max 340PC_Molecular device).

4) The data were analyzed.

The experimental results were shown in Table 6:

TABLE 5

Results of CPE assay EC$_{50}$/CC$_{50}$ Test

| Testing sample (The product obtained in the example) | CPE assay EC$_{50}$/CC$_{50}$(μM) | |
|---|---|---|
| | EC$_{50}$ | CC$_{50}$ |
| BMS433771 | 0.015 | >100 |
| Compound of formula (I) | 0.007 | >100 |

Note:
EC$_{50}$ indicates the anti-respiratory in vitro syncytial virus activity of the molecule; the CC$_{50}$ values indicate the in vitro toxicity of the molecule. the test was repeated n = 7 times
CONCLUSIONS: Compared with BMS433771, compound of formula (I) had better activity in vitro and both of them have no cytotoxicity.

Note: EC$_{50}$ indicates the anti-respiratory in vitro syncytial virus activity of the molecule; the CC$_{50}$ values indicate the in vitro toxicity of the molecule. the test was repeated n=7 times CONCLUSIONS: Compared with BMS433771, compound of formula (I) had better activity in vitro and both of them have no cytotoxicity.

What is claimed is:

1. A crystal form A of the compound of formula (I):

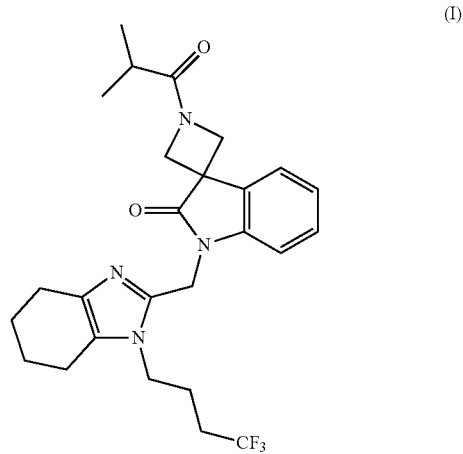 [SMILES: CC(C)C(=O)N1CC2(C1)C(=O)N(Cc1nc3c(n1CCCC(F)(F)F)CCCC3)c1ccccc12]

wherein the X-ray powder diffraction spectrogram of the crystal form A is shown in FIG. 1.

2. A pharmaceutical composition comprising a pharmaceutically acceptable carrier and a therapeutically effective amount of the crystal form A according to claim 1 as an active ingredient.

3. A method for inhibiting respiratory syncytial virus activity in a subject, comprising administering to the subject in need thereof a therapeutically effective amount of the crystal form A according to claim 1.

4. The method according to claim 3, wherein the subject has respiratory virus infection.

5. A method for inhibiting respiratory syncytial virus activity in a subject, comprising administering to the subject in need thereof a therapeutically effective amount of the pharmaceutical composition according to claim 2.

6. The method according to claim 5, wherein the subject has respiratory virus infection.

7. A process for preparing the crystal form A according to claim 1, wherein the process comprises the following steps:
(1) admixing the compound of formula (I) according to claim 1 with an organic solvent to form a mixture,
(2) heating the mixture formed in step (1) above to 30° C. to form a solution, and
(3) cooling the solution of step (2) above to a temperature in the range of 0° C. to 20° C. over a period of 0.5 hour to 10 hours to precipitate the crystal form A.

8. The process according to claim 7, wherein the organic solvent is selected from the group consisting of dichloroethane, a C$_{1-6}$ alkyl alcohol, a C$_{4-10}$ alkyl ether, a C$_{4-10}$ cycloalkyl ether, a C$_{2-6}$ alkyl ketone, a C$_{2-6}$ alkyl carboxylate ester and benzene substituted by 1, 2 or 3 substituents independently selected from the group consisting of methyl, ethyl and halogen.

9. The process according to claim 8, wherein the organic solvent is selected from the group consisting of dichloroethane, methanol, ethanol, isopropanol, tetrahydrofuran, 2-methyltetrahydrofuran, dioxane, acetone, ethyl acetate, isopropyl acetate, toluene, xylene and chlorobenzene.

* * * * *